US006087557A

United States Patent [19]
Clausen et al.

[11] Patent Number: 6,087,557
[45] Date of Patent: Jul. 11, 2000

[54] METHODS FOR THE MODULATION OF LIGNIFICATION LEVELS

[75] Inventors: Monika Clausen, Oldenburg, Germany; Christopher J. Lamb; Peter Doerner, both of San Diego, Calif.; Yonatan Elkind, Rehovot, Israel; Roland Megnet, Oldenburg, Germany

[73] Assignee: The Salk Institute for Biological Studies, La Jolla, Calif.

[21] Appl. No.: 07/957,941

[22] Filed: Oct. 6, 1992

[51] Int. Cl.[7] .............................. A01H 5/00; C12N 15/82
[52] U.S. Cl. ...................... 800/278; 800/298; 435/69.1; 435/468
[58] Field of Search ............................... 435/172.3, 69.1, 435/71.1, 91.1, 240.4, 257.3, 419, 468; 800/205, 298, 295, 278

[56] References Cited

U.S. PATENT DOCUMENTS

| | | | |
|---|---|---|---|
| 4,478,976 | 10/1984 | Goertz et al. | 525/54.1 |
| 4,710,467 | 12/1987 | Wood et al. | 435/108 |

FOREIGN PATENT DOCUMENTS

| | | |
|---|---|---|
| 2005597 | 6/1990 | Canada . |
| 0406760 | 1/1991 | European Pat. Off. . |

OTHER PUBLICATIONS

Beggs, "Transformation of yeast by a replicating hybrid plasmid," *Nature*, 275:104–109 (1978).
Bell, "Differential induction of chalcone synthase mRNA activity at the onset of phytoalexin accumulation in compatible and incompatible plant–pathogen interactions," *Proc. Natl. Acad. Sci. USA*, 81:3384–3388 (1994).
Benfey and Chua, "Regulated Genes in Transgenic Plants," *Science*, 244:174–181 (1989).
Bevan, "Binary Agrobacterium vectors for plant transformation," *Nucleic Acids Research*, 12:8711–8721 (1984).
Bradford, "A Rapid and Sensitive Method for the Quantitation of Microgram Quantities of Protein Utilizing the Principle of Protein–Dye Binding," *Analytical Biochemistry*, 72:248–254 (1976).
Carlson and Botstein, "Two Differentially Regulated mRNAs with Different 5' Ends Encode Secreted and Intracellular Forms of Yeast Invertase," *Cell*, 28:145–154 (1982).
Clausen et al., "Expression of the Phenylacrylic Acid Decarboxylase (PAD) in Transgenic Plants and its Effect on Development," Proceedings of the *Third International Congress of Plant Molecular Biology Molecular Biology of Plant Growth and Development*, Tucson (1991).
Cramer et al., "Phenylalanine ammonia–lyase gene organization and structure," *Plant Molecular Biology*, 12:367–383 (1989).
Dalkin et al., "Stress Responses in Alfalfa (*Medicago sativa* L.)," *Plant Physiol.*, 92:440–446 (1990).
Dixon and Bendall, "Changes in the levels of enzymes of phenylpropanoid and flavonoid synthesis during phaseollin production in cell suspension cultures of *Phaseolus vulgaris*," *Physiological Plant Pathology*, 13:295–306 (1978).

Edwards et al., "Rapid transient induction of phenylalanine ammonia–lyase mRNA in elicitor–treated bean cells," *Proc. Natl. Acad. Sci. USA*, 82:6731–6735 (1985).
Elkind et al., "Abnormal plant development and down–regulation of phenylpropanoid biosynthesis in transgenic tobacco containing a heterologous phenylalanine ammonia–lyase gene," *Proc. Natl. Acad. Sci. USA*, 87:9057–9061 (1990).
Gietz and Sugino, "New yeast–*Escherichia coli* shuttle vectors constructed with in vitro mutagenized yeast genes lacking six–base pair restriction sites," *Gene*, 74:527–534 (1988).
Goodey and Tubb, "Genetic and Biochemical Analysis of the Ability of *Saccharomyces cerevisiae* to Decarboxylate Cinnamic Acids," *Journal of General Microbiology*, 128:2615–2620 (1982).
Hoekstra et al., "Shuttle Mutagenesis: Bacterial Transposons for Genetic Manipulations in Yeast," *Methods in Enzymology*, 194:329–342 (1991).
Hoisington et al., "Disease Lesion Mimics in Maize," *Developmental Biology*, 93:381–388 (1982).
Ito et al., "Transformation of Intact Yeast Cells Treated with Alkali Cations," *Journal of Bacteriology*, 153:163–168 (1983).
Keller et al., "Specific localization of a plant cell wall glycine–rich protein in protoxylem cells of the vascular system," *Proc. Natl. Acad. Sci. USA*, 86:1529–1533 (1989).
Liang et al., "Differential Regulation of Phenylalanine Ammonia–Lyase Genes during Plant Development and by Enviromental Cues," *The Journal of Biological Chemistry*, 264:14486–14492 (1989).
Mason et al., "Cytochrome c Oxidase from Bakers' Yeast," *The Journal of Biological Chemistry*, 248:1346–1354.
Murashige and Skoog, "A Revised Medium for Rapid Growth and Bio Assays with Tobacco Tissue Cultures," *Physiologia Plantarum*, 15:473–497 (1962).

(List continued on next page.)

*Primary Examiner*—Elizabeth F. McElwain
*Attorney, Agent, or Firm*—Gary Cary Ware & Friedenrich; Stephen E. Reiter

[57] ABSTRACT

In accordance with the present invention, there are provided methods to modulate plant lignification. For example, the level of the enzyme phenylalanine ammonia-lyase (PAL), a key enzyme in the production of lignin precursors, can be increased or decreased, as desired, to increase or decrease lignification levels. Alternatively, the level of lignin precursors in the plant can be modulated either by enhancing the plant's ability to produce such precursors, or by causing the compounds which are required for the production of lignin precursors to undergo alternative chemical conversions (which prevent the incorporation of such compounds into lignin by diverting the lignin precursors to other chemical pathways). In addition, there is provided a method for producing plants having modified lignin composition and content, by converting a portion of the cinnamic acid in said plant to styrene. In another embodiment, there is provided a method for producing styrene and/or styrene derivatives, by contacting cinnamic acid or a cinnamic acid derivative with PAD under decarboxylation conditions.

2 Claims, 3 Drawing Sheets

OTHER PUBLICATIONS

Murray and Thompson, Rapid Isolation of high molecular weight plant DNA, *Nucleic Acids Research*, 8:4321–4325 (1980).

Oberto and Davison, "Expression of chicken egg white lysozyme by *Saccharomyces cerevisiae*," *Gene*, 40:57–65 (1985).

Perlman and Mahler, "Intracellular Localization of Enzymes in Yeast," *Archives of Biochemistry and Biophysics*, 136:245–250 (1970).

Polakis and Bartley, "Changes in the Enzyme Activities of *Saccharomyces cerevisiae* during Aerobic Growth on Different Carbon Sources," *Biochem. J.*, 97:284–297 (1965).

Rogers et al., "Gene Transfer in Plants: Production of Transformed Plants Using Ti Plasmid Victors," *Methods in Enzymology*, 118:627–640 (1986).

Rose and Botstein, "Construction and Use of Gene Fustions to lacZ (β–Galatosidase) That Are Expressed in Yeast," *Methods in Enzymology*, 101:167–181 (1983).

Saiki et al., "Primer–Directed Enzymatic Amplification of DNA with a Thermostable DNA Polymerase," *Science*, 239:487–491 (1988).

Snook et al., "Polyphenols in the Nicotiana Species," *Tobacco Science*, 30:43–49 (1985).

Valvekens et al., "*Agrobacterium tumefaciens*–mediated transformation of *Arabidopsis thaliana* root explants by using kanamycin selection," *Proc. Natl. Acad. Sci. USA*, 85:5536–5540 (1988).

Grunewald et al., "Conformationally Defined Aromatic Amino Acids. Synthesis and Stereochemistry of 2–endo–and 2–exo–Amino–1,2,3,4–tetrahydro–1,4–ethanonapthalene–2–carboxylic Acids (2–endo–and 2–exo–Aminobenzobicyclo[2.2.2]octene–2–carboxylic Acids)" *J. Med. Chem.* 23(7):754–758 (1980).

Shields et al., "Dual Control of Phenylalanine Ammonia-Lyase Production and Removal by Its Product Cinnamic Acid" *Euro. J. Biochem.* 123:389–395 (1982).

Finnegan et al. (1994) Bio/Technology 12:883–888.

Struhl (1983) Nature 305:391–397.

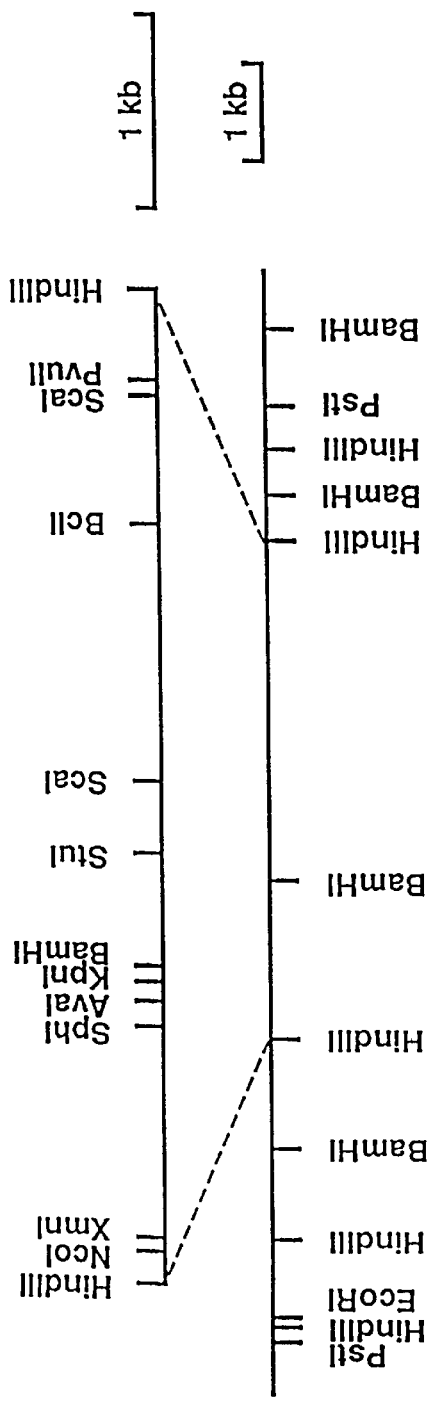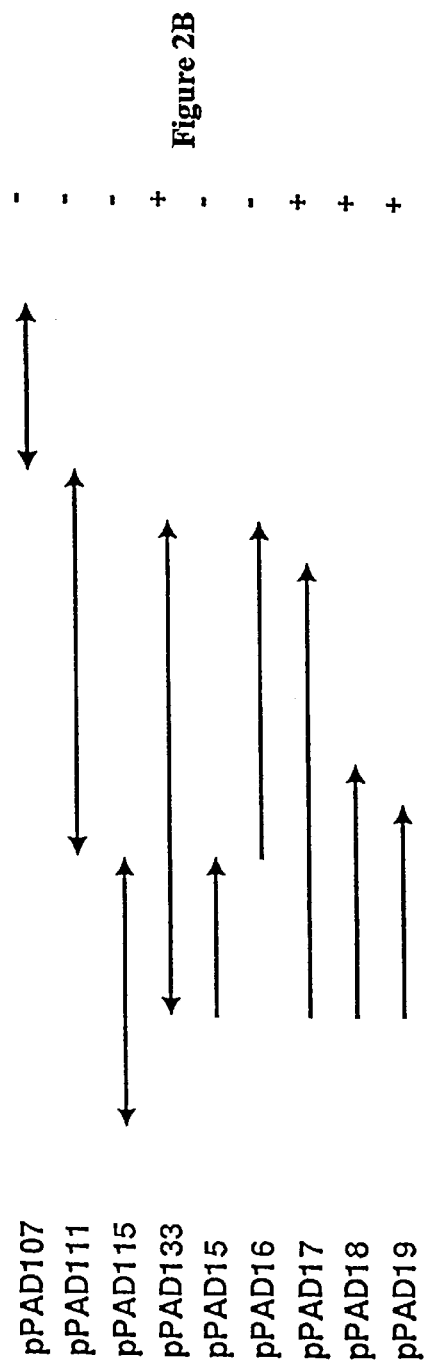
Figure 2A
Figure 2B

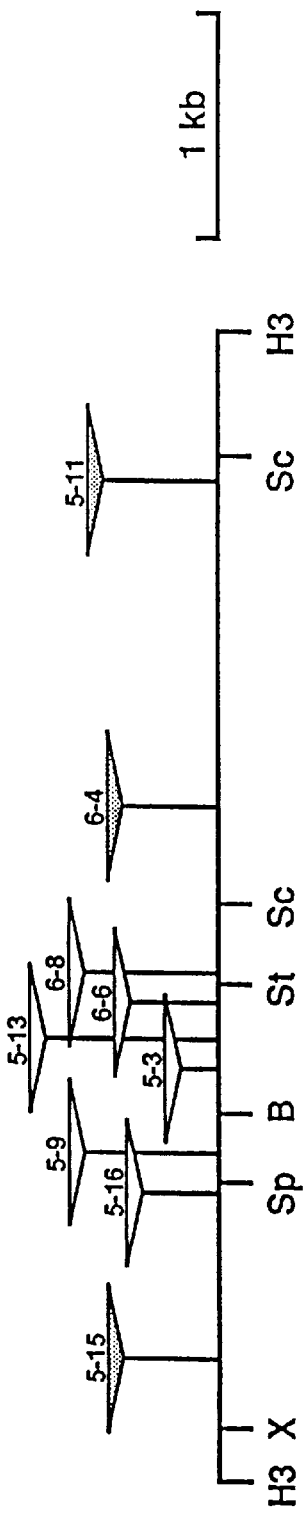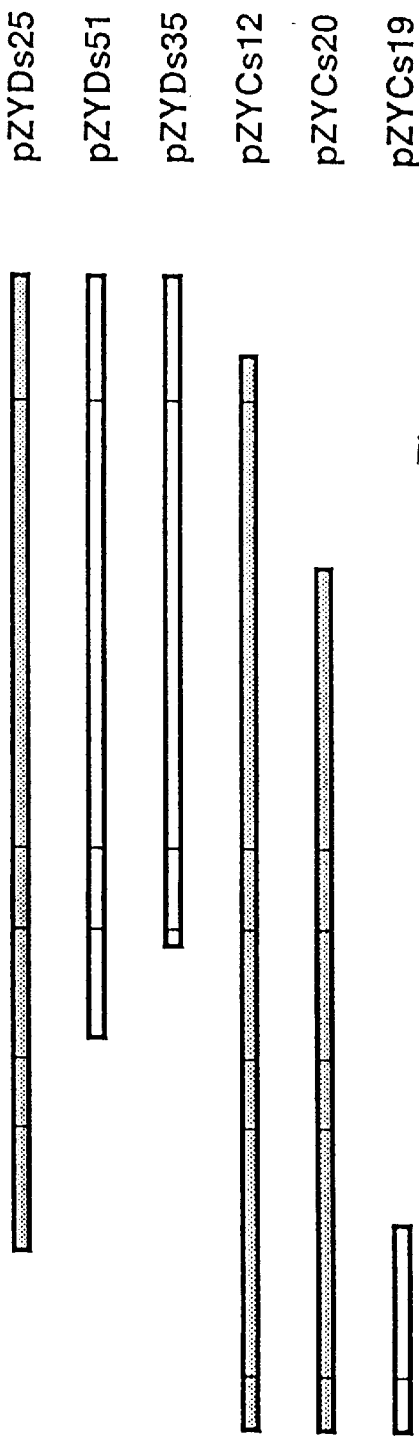
Figure 3A
Figure 3B

METHODS FOR THE MODULATION OF LIGNIFICATION LEVELS

FIELD OF THE INVENTION

The present invention relates to genetic engineering of plants. In a particular aspect, the present invention relates to methods for modulating (i.e., increasing or decreasing) lignification levels of plants.

BACKGROUND OF THE INVENTION

Lignin is a complex polymer composed mainly of $C_6$–$C_3$ units derived from coniferyl and sinapyl alcohols. Lignin can be regarded as nature's version of the reinforcing steel used in modern building construction, as it provides the strength needed to support the vertical growth of plants and trees.

In order to impart improved strength to plants, it may be desirable to be able to enhance the lignification levels of plants, thereby providing plants more able to resist certain external forces (such as high winds, heavy rains, etc.).

In other situations, where plant strength is not a particular concern, it may be desirable to reduce the lignification levels of a plant to improve the digestability thereof (e.g., with forage crops), to improve the ease of handling (e.g., with cereal crops), and the like.

The production of lignin by plants is a complex process, believed to involve the oxidative dimeization (or polymerization) of phenylpropanoid compounds. The phenylpropanoid route to lignins involves the conversion of shikimic acid to phenylalanine (or tyrosine), which is in turn converted to cinnanic acid (or p-coumaric acid), which is believed to be a precursor to lignin. As noted above, in different situations, it would be desirable to be able to enhance the lignin-forming process, or depress the lignin forming process.

BRIEF DESCRIPTION OF THE INVENTION

In accordance with the present invention, we have developed methods to modulate plant lignification. For example, the level of the enzyme phenylalanine ammonia-lyase (PAL), a key enzyme in the production of lignin precursors, can be increased or decreased, as desired, to increase or decrease lignification levels. Alternatively, the level of lignin precursors in the plant can be modulated either by enhancing the plant's ability to produce such precursors, or by causing the compounds which are required for the production of lignin precursors to undergo alternative chemical conversions (which prevent the incorporation of such compounds into lignin by diverting the lignin precursors to other chemical pathways).

Decreased lignin content plants are desirable as they provide forage crops having increased digestability, thereby providing the animal with more nutrients per unit of forage. The effective biomass of a plant is thereby increased by the reduction of lignin content.

Increased lignin levels are desirable as they provide plants having increased sturdiness, thereby reducing the likelihood of plant losses due to "lodging", thereby reducing the likelihood of plant losses due to mechanical damage to the aerial parts of the plant.

Plants expressing increased PAL activity are desirable as they would possess a higher level of resistance to attack by plant pathogens.

BRIEF DESCRIPTION OF THE FIGURES

FIGS. 2A and 2B present a restriction and complementation analysis, respectively, of cloned yeast sequences derived from the phenylalanine decarboxylase locus. FIG. 2A shows the restriction analysis. FIG. 2B shows the analysis of complementation of cloned yeast sequences to PAD. Bidirectional arrows in FIG. 2B indicate that complementation analysis was performed with inserts cloned in both orientation. += complementation and −= no complementation.

FIGS. 3A and 3B present an analysis of sequences containing phenylalanine decarboxylase encoding activity, showing the localization of PAD activity on a 5.1 kb HindIII fragment of yeast DNA.

DETAILED DESCRIPTION OF THE INVENTION

Figure 1:
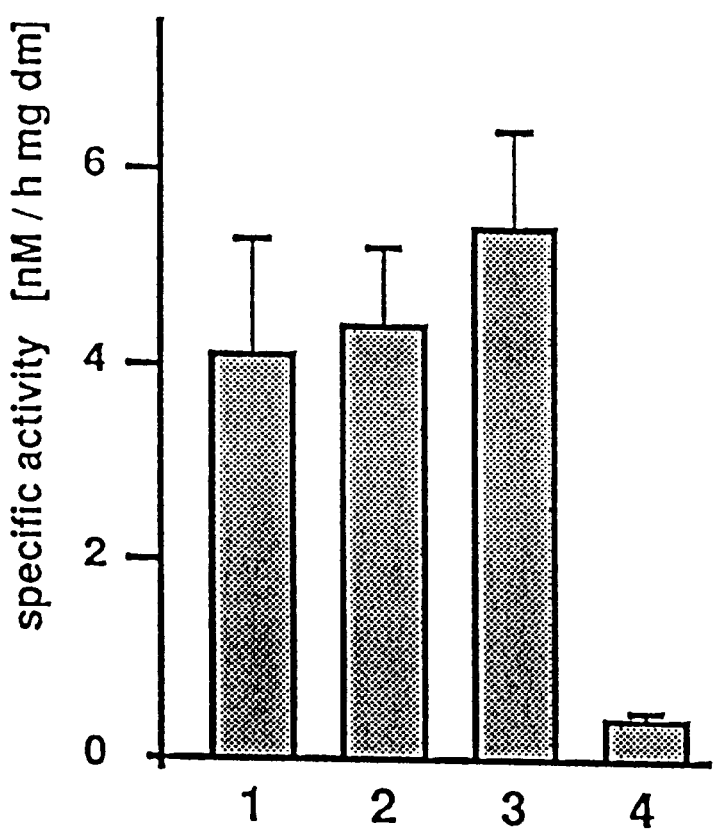
FIG. 1 illustrates the enzyme activity of yeast phenylalanine decarboxylase (PAD) with a variety of substrates. Column 1=styrene; Column 2=4-OH styrene; Column 3=4-OH, 3-$OCH_3$ styrene; and Column 4=2-OH styrene.

In accordance with the present invention, there are provided methods of modulating plant lignification, by altering the flux of lignin precursors feeding into the lignification pathway in the plant, and/or by altering the level or composition of lignin precursors present in the plant.

As employed herein, the phrase "lignin precursors" refers to all of the various chemical compounds which can ultimately become incorporated into lignin, as well as the various enzymes involved in converting such compounds into lignin or directing such compounds along the lignin-forming pathway (e.g., phenlalanine ammonia-lyase, PAL). Exemplary lignin precursor compounds include shikimic acid, phenylalanine, cinnamic acid, cinnamyl alcohol, p-coumaric acid, p-coumaryl alcohol, ferulic acid, ferulyl alcohol, caffeic acid, sinapyl alcohol, and the like.

In accordance with one embodiment of the present invention, there are provided methods for reducing plant lignification, said methods comprising reducing the level of lignin precursors in said plant.

In accordance with a specific aspect of the invention, the level of lignin precursors in said plant is decreased by blocking the production thereof (e.g., by introducing into said plant antisense RNA complementary to PAL-encoding RNA, thereby blocking the production of the lignin precursor, PAL), or by further converting such precursors before they can be incorporated by the plant into lignin (e.g., by introducing PAD enzyme into said plant), or by combinations of such methods.

In accordance with another embodiment of the present invention, there is provided a method for increasing plant lignification, said method comprising:

(1) causing the over-expression of PAL enzyme by said plant; and (2) maintaining said plant under conditions suitable for growth.

In accordance with this aspect of the present invention, the level of endogenous PAL enzyme in said plant is altered by causing the over-expression thereof. This can be achieved in a variety of ways, e.g., by the introduction of an exogenous PAL-encoding construct into said plant; by placing endogenous PAL-encoding DNA under the control of a highly expressed, optionally inducible promoter, such as, for example, the 35S promoter, the chalcone synthase promoter, the 4-coumarate:CoA ligase promoter, the rubisco (i.e., ribulose bisphosphate carboxylase oxidase) promoter, and the like; excluding the use of the constitutive, non-specific promoter 35S, in combination with a truncated form of the PAL promoter, as described by Elkind et al., in Proc. Natl. Acad. Sci. USA 87:9057–9061 (1990).

In accordance with still another embodiment of the present invention, there is provided a method for producing plants having modified lignin composition and content, said method comprising converting a portion of the cinnamic acid in said plant to styrene.

Plants having modified lignin composition and/or content are those wherein the chemical nature of the lignin is modified (relative to lignin produced by wild-type plant), and/or the lignin content of the plant is modified (increased or decreased, relative to lignin levels in wild-type plant). The chemical nature of lignin can be modified by promoting chemical modification of one or more lignin precursors prior to incorporation into the lignin polymer.

In accordance with a further embodiment of the present invention, there is provided a method for producing styrene and/or styrene derivatives, said method comprising contacting cinnamic acid or a cinnamic acid derivative with PAD under decarboxylation conditions.

Cinnamic acid derivatives contemplated for use in the practice of the present invention include ring-substituted derivatives of cinnamic acid such as:

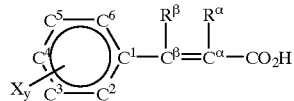

wherein:
X is an optional substituent on $C^3$, $C^4$, or $C^5$, and each X is independently selected from hydroxy, alkoxy, alkyl, amino, carboxy, nitro, or halogen;
y falls in the range of 0 up to 3;
$R^\alpha$ is selected from H, a halogen or a $C_1$–$C_{12}$ alkyl radical; with $R^\alpha$ preferably being H, and
$R^\beta$ is selected from H, a halogen or a $C_1$–$C_6$ alkyl radical; with $R^\beta$ preferably being H.

Examples of cinnamic acid derivatives contemplated for use in the practice of the present invention include:
3-amino cinnamic acid, 4-amino cinnamic acid,
3-hydroxy cinnamic acid, 4-hydroxy cinnamic acid (i.e., p-coumaric acid),
3-methoxy cinnamic acid, 4-methoxy cinnamic acid,
4-isopropyl cinnamic acid,
3-carboxy cinnamic acid, 4-carboxy cinnamic acid,
3-nitro cinnamic acid, 4-nitro cinnamic acid,
3,4-dihydroxy cinnamic acid (i.e., caffeic acid), 3,5-dihydroxy cinnamic acid,
3,4-dimethoxy cinnamic acid, 3,5-dimethoxy cinnamic acid,
3,4,5-trimethoxy cinnamic acid,
3,5-dimethoxy-4-hydroxy cinnamic acid,
α-bromo cinnamic acid, β-bromo cinnamic acid,
α,β-dibromo cinnamic acid,
α-methyl cinnamic acid,
α-ethyl cinnamic acid,
4-hydroxy-3-methoxy cinnamic acid (i.e., ferulic acid),
α-methyl-3-nitro cinnamic acid,
4-methyl-3-nitro cinnamic acid,
α-methyl-4-nitro cinnamic acid,
and the like.

Presently preferred cinnamic acid derivatives contemplated for use in the practice of the present invention include:
3-hydroxy cinnamic acid, 4-hydroxy cinnamic acid (i.e., p-coumaric acid),
3,4-dihydroxy cinnamic acid (i.e., caffeic acid),
3-methoxy cinnamic acid, 4-methoxy cinnamic acid,
3-nitro cinnamic acid, 4-nitro cinnamic acid,
3,5-dimethoxy-4-hydroxy cinnamic acid,
4-hydroxy-3-methoxy cinnamic acid (i.e., ferulic acid),
and the like.

In accordance with a further aspect of this embodiment of the present invention, the PAD can be immobilized and said cinnamic acid or cinnamic acid derivative then brought into intimate contact with the immobilized PAD, e.g., by passing the cinnamic acid or derivative thereof over a packed column of immobilized enzyme. In accordance with a still further aspect of the present invention, the cinnamic acid or cinnamic acid derivative is prepared by contacting phenylalanine with immobilized PAL.

The PAD enzyme employed in the practice of the present invention can be obtained from a variety of sources, as can be readily determined by one of skill in the art. A presently preferred source of PAD is from a unicellular organism, especially when recombinantly expressed by a unicellular organism. A particularly preferred unicellular organism is one which further expresses PAL, especially where such organism is also capable of over-expressing phenylalanine.

The invention will now be described in greater detail by reference to the following non-limiting examples.

EXAMPLES

Example 1

PAL2 Expression Vectors

An expression cassette pYE1, consisting of a cauliflower mosaic virus 35S enhancer element and nopaline synthase 3' flanking sequences was constructed from pBI221 [Bevan, Nucleic Acids Res. Vol. 12:4321–4325 (1984)] cut with EcoRV and SacI and ligated to the SalI (filled-in with Klenow)/SacI fragment of the pUCl9 polylinker). The 5.3 kilobase (kb) PAL2 gene [see Cramer et al., in Plant Mol. Biol. Vol. 12:367–383 (1989)], including 1170 base pairs (bp) of 5' flanking sequence was used to generate two exonuclease III 5' deletions with end points at −613 and −235 relative to the transcription start site. These promoter deletions were cut with EcoRI and HindIII, and the ends were filled in and ligated into pYE1 cut with SmaI to give pYE2 and pYE4, respectively, containing the −89 to −800 35S enhancer, the PAL2 gene with the respective 5' promoter deletion, and nopaline synthase 3' flanking sequences. These constructs were excised from pYE2 and pYE4 by PvuII and cloned into the SmaI site of Bin19 [Bevan, Nucleic Acids Res. Vol. 12:8711-8721 (1984)] to give pYE6 and pYE11, respectively. pYE10 contains a tandem duplication of the PvuII fragment of pYE4.

Example 2

Plant Transformation pYE6, pYE10, and pYE11 were mobilized into *Agrobacterium tumefaciens* strain LBA 4404 [Bevan, supra] and transgenic tobacco (*Nicotiana tabacum* cv. Xanthi) plants were generated by the leaf disk method [Rogers et al., Methods Enzymol. Vol. 118:627–640 (1986)]. Transformed plants were selected on Murashige and Skoog (MS) medium [Murashige and Skoog, Physiol. Plant Vol. 15:473–497 (1962)] containing kanamycin at 200 μg/ml and carbenicillin or cefatoxin at 500 μg/ml. Transgenic plants were grown under greenhouse conditions at 18±5° C. (night) and 27±5° C. (day). Transgenic plant ($T_1$) YE6-16 was selfed and seeds were collected. Progeny ($T_2$) were selfed and their genotypes were determined by progeny ($T_3$) analysis. $T_3$ seeds were germinated on MS basal medium containing kanamycin (200 μg/ml). After 2–4 weeks, kanamycin-resistant plants had green leaves, whereas sensitive seedlings had bleached leaves.

Example 3

Nucleic Acid Analysis

DNA was isolated from tobacco leaves by the cetyltrimethylammonium bromide procedure [see Murray and Thompson, in Nucleic Acids Res. Vol. 8:4321–4325 (1980)]. RNA was extracted by phenol extraction and isolated as described by Bell et al., in Proc. Natl. Acad. Sci. USA Vol. 81:3384–3388 (1984). Blot hybridizations and other standard manipulations were carried out as described by Sambrook et al., Molecular Cloning: A Laboratory Manual (Cold Springs Harbor Lab., Cold Springs Harbor, N.Y.), 2nd ed. (1989). A tobacco PAL gene sequence was amplified from tobacco genomic DNA by the polymerase chain reaction [Saiki et al., Science Vol. 239:487–491 (1988)] with partially degenerate primers corresponding to the GRIFEILEA (SEQ ID NO:1) and QIEAAAIME (SEQ ID NO:2) peptides conserved in the family of bean PAL genes [Cramer et al. supra].

The amplified sequence was cloned in pSP64 (Promega Biotec) to give pPAL-Nt, and its identity was confirmed by nucleotide sequencing [Sambrook et al., supra] and comparison of the deduced amino acid sequences with bean PAL (81% and 71% similarities to bean PAL2 at the amino acid and nucleotide levels, respectively). pSPP2 contains a 1.64 kb EcoRI/NarI fragment of the bean PAL2 gene, comprising 327 bp of the first exon, the 115 bp 5' untranslated region, and 1.2 kb of the 5' flanking sequence cloned in pSP64 [Liang et al., J. Biol. Chem. Vol. 264:14486–14492 (1989)].

The in vitro transcribed antisense products of pPAL-Nt and pSPP2 were used as probes to monitor the levels of tobacco PAL transcripts and bean PAL2 transcripts, respectively, in RNase protection experiments [Liang et al. supra]. Nick-translated insertion sequences from the bean pPAL5 cDNA [Edwards et al., Proc. Natl. Acad. Sci. USA Vol. 82:6731–6735 (1985)] and pPAL-Nt were used to probe Southern blots of genomic DNA [Sambrook et al., supra].

Example 4

Enzyme Activity

Flowers and leaf tissue were collected and snap frozen in liquid $N_2$. Leaves of vegetatively propagated plants were harvested from YE6-16 plants at the onset of flowering, and from control and YE10-6 plants of the same age. In YE6-16 $T_2$ progeny, the seventh fully expanded leaf was collected from 9-week-old plants and 2 weeks later the leaf above it was collected. Petals were collected from flowers 1 day before anthesis. PAL activity was measured in cell extracts by a radiometric assay [see Dixon and Bendall, in Physiol. Plant Pathol. Vol. 13:295–306 (1978)].

Example 5

Phenolic Analysis

Leaf samples (0.1 g) were homogenized in ice-cold acetonitrile (4 ml) after spiking the sample with [$^{14}$C] cinnamic acid (14 KBq (kiloBecquerel), 0.7 nmol) synthesized as described by Dalkin et al., in Plant Physiol. Vol. 92:440–446 (1990). After centrifugation, the residue was re-extracted in 50% (vol/vol) aqueous acetonitrile (4 ml) and the combined extracts were evaporated to 2 ml under reduced pressure. The concentrate was acidified to pH 2 with 1 M HCl and applied to a C-18 Sep Pak cartridge (Waters). After washing with 0.01 M HCl, the phenolic fraction was recovered by eluting the Sep Pak with 2 ml of water plus acetonitrile (6:4; vol/vol). The sample was concentrated to 0.2 ml and 20 μl was analyzed by HPLC using an octadecyl column (250×4.6 mm) with 5 μm packing and eluted at 1 ml/min with a four-step gradient of increasing solvent B in solvent A [i.e., step 1 employed 5% B for 5 min, step 2 involved increasing to 5–10% B for 5 min, step 3 involved further increasing to 10–15% B for 15 min, and step 4 involved finally increasing to 35–40% B for 5 min]. Solvent A was water/formic acid (98:2; vol/vol) and solvent B was acetonitrile/formic acid (98:2; vol/vol). Eluant was monitored for UV absorbance at 271 and 340 nm and for radioactivity by scintillation counting. Recoveries of the internal standard [$^{14}$C] cinnamic acid were 65%±17% (n=8), and corrections for losses were made for the individual samples by using the internal standard.

Example 7

Histochemistry

Lateral cross-sections (10 μm) of stems were prepared as described by Keller et al., in Proc. Natl. Acad. Sci. USA Vol. 86:1529–1533 (1989)] and either stained with toluidine blue and examined in bright field with a Nikon Diaphot TMD microscope or examined for UV fluorescence with the same microscope in the fluorescence mode.

Example 8

Phenotypes of transgenic plants

In bean, PAL2 transcripts are found at very high levels during floral development and also accumulate in roots and stems [see Liang et al., supra]. To facilitate expression of the heterologous PAL2 gene in tobacco, the −89 to −800 enhancer element of the cauliflower mosaic virus 35S promoter [see Benfey and Chua, in Science Vol. 244:174–181 (1989)] was substituted for the sequences between −1170 and either −550 (pYE6) or −270 (pYE10, pYE11) in the PAL2 promoter. The phenotypes of transgenic plants containing these constructs fell into three classes: class I (15 of 23 independent transformants) showed no visible differences from wild type: class II (6 transformants) had altered flowers; and class III (2 transformants) showed abnormal vegetative as well as floral development.

Class III transformants (YE6-16 and YE10-6) were stunted. Their leaves were curled showing spoon-like, epinastic growth and localized lesions, and had a rough texture. The leaves developed localized UV-fluorescent lesions, which resembled those in disease lesion mimic mutants [see Hoisington et al., in Dev. Biol. Vol. 93:381–388 (1982)]. The walls of stem xylem cells were thinner and contained markedly less lignin than wild type as monitored by either histochemical staining of cross-sections with toluidine blue, which stains lignin light blue, or by UV fluorescence.

Plants vegetatively propagated from transformant YE10-6 had not flowered after 1 year. In YE6-16, the flowers were shorter and thicker than wild type, the filaments were shorter, less pollen was produced, pollen viability was severely reduced, and the anthers tended to abort. Most strikingly, some petals were white, and others showed a gradient of pink anthocyanin pigment accumulation, from wild-type levels at the edge of the petal to very low levels in internal regions adjacent to veins. The flowers of class II transformants showed some of these features, including similar changes in pigmentation patterns and levels and reduced amounts of viable pollen.

Example 9

Inheritance of exogenous sequences

The phenotypes appear stable and no revertants of YE6-16 have been found. However, expression of the phenotypes was affected by the environment, such that growth of plants at higher temperatures and light intensities promoted the development of more pronounced symptoms. Southern blots of DNA from YE6-16 and YE10-6 and selected class I and class II plants probed with tobacco PAL sequences showed that there were no changes in the organization of the endogenous family of five or six tobacco PAL genes. The same blots probed with bean PAL2 sequences suggested that the transgene was inserted at different sites in the genome in these independent transformants. The segregation for kanamycin resistance in $T_2$ progeny of selfed YE6-16 was 203 resistant and 63 sensitive, indicating a single insertion. Southern blot analysis of 13 individual $T_2$ plants showed that hybridizable bean PAL2 sequences cosegregated with kanamycin resistance (Table 1).

The presence of the transgene was determined by probing Southern blots of genomic DNA with bean PAL2 sequences and by resistance to kanamycin, which cosegregated in the YE6-16 $T_2$ progeny. The genotypes of individual $T_2$ plants were determined by analysis of the segregation of kanamycin resistance in selfed progeny ($T_3$). PAL activities and symptom development (scale of 0.5) were examined in each of the four or five independent PAL2/PAL2 homozygotes, PAL2/+ heterozygotes, and +/+ homozygotes compared to control, wild-type plants. The development of symptoms such as leaf curling and fluorescent lesions differed significantly in the different $T_2$ genotypes: plants homozygotic for the transgene exhibited markedly more severe symptoms than the heterozygotes, while progeny lacking the transgene showed no symptoms at all (Table 1). Thus, symptom development was inherited as a single, partially dominant trait that absolutely cosegregated with the PAL2 transgene. PAL activities are presented as the mean ±SE.

Example 10

PAL Activity and Phenylpropanoid Accumulation

The low level of lignin and the altered pattern of flower pigmentation suggested that introduction of the bean PAL2 gene paradoxically reduced phenylpropanoid synthesis. In line with this hypothesis, the levels of extractable PAL activity were markedly reduced in leaves and flowers of the class III transformants. Thus, PAL activities in YE6-16 petals and anthers were 2.6 and 0.1 nmol of product per hr per kg of protein compared with 11 and 5.6, respectively, in wild-type flowers. Likewise, PAL activities in mature leaves of the YE6-16 and YE10-6 primary transformants ($T_1$) were 0.07 and 0.02 nmol per hr per kg of protein compared with 1.5 nmol in wild-type plants. Wounding of leaf tissue from YE6-16 and YE10-6 plants increased PAL activity to 1.5 and 0.26 nmol of product per hr per kg of protein, respectively, compared to 5.4 nmol in wounded leaves from control plants. Thus, although the transformants responded to this environmental stimulus, the induced PAL activity remained severalfold lower than in comparably treated wild-type plants.

In the $T_2$ progeny of selfed YE6-16, severely reduced levels of PAL activity were observed in the leaves and flowers of plants that contained the transgene and exhibited symptoms, with normal levels of PAL activity in symptomless progeny not containing the transgene (see Table 1). Moreover, PAL activity was substantially lower in the $T_2$ plants homozygous for the transgene compared to the heterozygotes (see Table 1), indicating that the reduction of PAL activity was inherited in the same manner as visible symptoms, i.e., as a single, partially dominant trait.

The leaves of YE6-16 and YE10-6 $T_1$ plants exhibited a qualitative profile of soluble phenolic products very similar to that from wild-type plants. However, the levels of these products were substantially lower. HPLC analysis of soluble phenolic products from leaves of YE6-16 $T_2$ plants shows, as expected, that leaves of symptomless $T_2$ plants showed no appreciable quantitative difference in the profile of soluble phenolic compounds compared to leaves of wild-type plants, whereas leaves of $T_2$ plants showing symptoms had severely reduced levels of phenolic compounds. Chlorogenic acid (3-caffeoylquinic acid) and rutin (quercitin 3-$\beta$-D-rutinoside), two major phenylpropanoid products of tobacco leaves [see Snook et al., Tob. Sci. Vol. 33:43–49 (1986)] were identified by HPLC. In $T_2$ plants showing severe

TABLE 1

PAL activity and symptom development in YE6-16 progeny

| Parent plant | Bean PAL2 transgene | Genotype | No. of progeny | PAL activity, nmol of product per hr per kg of protein | | | Symptom Severity Leaves | |
|---|---|---|---|---|---|---|---|---|
| | | | | Leaves | | | 11 week | 12 week |
| | | | | 9 week | 11 week | Petals | | |
| YE6-16 | + | PAL2/PAL2 | 5 | 0.9 ± 0.1 | 0.2 ± 0.06 | 1.3 ± 0.1 | 3 | 3.6 |
| YE6-16 | + | PAL2/+ | 4 | 1.5 ± 0.2 | 0.4 ± 0.05 | 3.0 ± 0.3 | 1 | 1 |
| YE6-16 | − | +/+ | 4 | 3.0 ± 0.3* | 1.9 ± 0.15* | 24.6 ± 1.2* | 0 | 0 |
| Control | − | Wild type | 5 | 3.1 ± 0.3* | 1.7 ± 0.16* | 23.9 ± 1.8* | 0 | 0 |

*Mean PAL activities in the same column are not significantly different (P = 0.01) in multiple range tests made on a logarithmic scale.

symptoms, the level of chlorogenic acid was 0.5±0.3 pmol/g fresh weight (mean ±SE of n>3 independent determinations) compared to 34±9.6 in symptomless $T_2$ plants and 38.4±5.0 in wild-type plants. Likewise, the level of rutin in $T_2$ plants showing severe symptoms was 0.3±0.0 pmol/g fresh weight, compared to 3.6±1.2 in symptomless $T_2$ plants and 3.7±1.0 in wild-type plants.

Example 11

Bean PAL2 and Tobacco PAL mRNA Levels

RNase protection experiments with a bean PAL2 sequence as probe showed that the transcript encoded by the transgene accumulated to high levels in leaves of YE6-16 and YE10-6 plants.

PAL mRNA levels for wound-induced bean hypocotyls, wild type tobacco leaves, leaves of YE10-6, and leaves of YE6-16 were determined. Probes used for RNase protection analysis of bean PAL2 mRNA (A) and endogenous tobacco PAL mRNA (B) levels, respectively, were antisense transcript synthesized in vitro from pSPP2 (which contains a region of the coding sequences of the bean PAL2 gene); antisense transcript was synthesized in vitro from pPAL-Nt (which contains a PAL gene sequence amplified from tobacco genomic DNA and cloned into pSP64).

The level of PAL2 mRNA in these transgenic tobacco plants was only 2–3 times lower than in wound-induced bean hypocotyls, where the endogenous PAL2 gene is very strongly expressed [Liang et al. supra]. No signal was observed when the bean PAL2 sequence was used to probe RNA from leaves of wild-type tobacco.

For analysis of transcripts encoded by endogenous tobacco PAL genes, a probe corresponding to a PAL gene sequence amplified from wild-type tobacco genomic DNA was used. RNA from leaves of wild-type tobacco contained appreciable levels of both the corresponding PAL transcript, which gave complete protection against RNase, and also several other tobacco PAL transcripts, which gave partial protection of the probe and which are presumably encoded by other members of the gene family. In contrast, almost no protection was observed with RNA isolated from leaves of YE10-6 and YE6-16, indicating that the family of tobacco PAL transcripts did not accumulate in leaves of these transgenic plants expressing the bean PAL2 transgene. RNA from wound-induced bean hypocotyls gave no protection, confirming the specificity of this probe for tobacco PAL transcripts.

Example 12

Cloning of yeast PAD gene a) Strains, plasmids and media

Strains and plasmids employed for the cloning of yeast PAD gene are listed in Table 2. *E. Coli* strains were grown either on LB [Maniatis et al., Molecular Cloning, Cold Spring Harbor Laboratory, Cold Spring Harbor, N.Y. (1982)] or M10 [Schleif and Wensink, Practical Methods in Molecular Biology, Springer, N.Y. (1981)], supplemented with antibiotics or amino acids as suggested by Schleif and Wensink supra. The recA1 mutation was introduced into AMA 1004 by mating with KL 16-99, giving rise to PDC75.

Complete medium for yeast was YEP [see Sherman et al., in Methods in yeast genetics, Cold Spring Harbor Laboratory, Cold Spring Harbor, N.Y. (1983)] with either 2% glucose or 3% glycerol as carbon source. For discrimination between the resistant and sensitive phenotype, 2% malt extract, pH 4.8, 0.2% glucose, with or without 0.6 mM t-cinnamic acid was used. Minimal medium was YM [see Croft and Jinks Practical Genetics, Sheppard, P.M. (ed), Blackwell Scientific, Oxford pp 173–224 (1973)] with supplements and amino acids added as suggested by Sherman et al. supra.

TABLE 2

Strains and plasmids

| Strain or plasmid | Genotype or description | Source or Reference |
|---|---|---|
| *E. coli* strains | | |
| DH1 | F$^-$, gyrA 96, recA 1, endA 1, thi 1, hsdR 17 (r$^-$, m$^+$), supE 44 | Hanahan (1983) |
| AMA 1004 | strA$^r$, hsdR$^-$, trpC 9830, leuB 6, Δ (lac IPOZ) C 29, lacY$^+$, recA$^+$ | Casadaban et al. (1983) |
| KL 16-99 | Hfr, recA 1, str$^s$ | Low (1968) |
| RDP146 | F$^-$, recA1, (Δlac—pro), rpsE, spec$^r$ | Hoekstra et al. (1991) |
| NS2114Sm | F$^-$, recA, rpsL, str$^r$, (contains λ-cre lysogen) | Hoekstra et al. (1991) |
| PDC75 | same as AMA 1004, but recA 1 | This work |
| *S. cerevisiae* strains | | |
| GRF18 | α, leu2-3, 2-112; his43-11, 3-15; PAD1 | gift of A. Hinnen |
| 6657-9B | a, leu2-3, 2-112; his4Δ34; PAD1 | gift of A. Hinnen |
| a ura3 ws | a, ura3 triple mutant | gift of F. Lacroute |
| z07 | α, leu2-3, 2-112; his3-11, 3-15; pad1-7 | This work |
| z042 | α, leu2-3, 2-112; his3-11, 3-15; pad1-42 | This work |
| z049 | α, leu2-3, 2-112; his3-11, 3-15; pad1-49 | This work |
| z0107 | α, leu2-3; 2-112; his3-11, 3-15; pad1-107 | This work |
| z0124 | α, leu2-3, 2-112; his3-11, 3-15; pad1-124 | This work |
| PDY102 | α, ura3, pad1-42 | This work |
| YPH501 | a/α, ura3-52/ura3-52, lys2-801$^{amber}$/lys2-801$^{amber}$, ade2-101$^{ochre}$/ade2-101$^{ochre}$, trp1-Δ63/trp1-Δ63, his3Δ200/his3Δ200, leu2Δ1/leu2Δ1 | Sikorski and Heiter (1989) |
| Plasmids | | |
| pLB101 | Cm$^r$, expresses Tn3 transposase constitutively | Hoekstra et al. (1991) |
| pOX38::mTn3-LEU2 | conjugative F factor derivative, carries mini-Tn3 with LEU2 insert | Hoekstra et al. (1991) |
| YEp24 | Ap$^r$, Tc$^r$, URA3, 2μ ori | Carlson and Botstein (1982) |
| pDB262 | Tc$^{s/r}$, λ cI P$_{RM}$, 2μ ori, LEU 2 | Beach et al. (1982) |
| pEMBLY23 | Ap$^r$, lac POZ, f1 ori 2μ ori, URA3 | Baldari and Cesareni (1985) |
| YEplac181 | Ap$^r$, 2μ ori, LEU2 | Gietz and Sugino (1988) |
| YEpZ100 | Ap$^r$, lacZ fusion vector, 2μ ori, LEU2 | Oberto and Davison (1985) |
| pHSS8 | Kan$^r$, ColE1 ori, pUC9 MCS | Hoekstra et al. (1991) |
| YCF3 | Ap$^r$, URA3, SUP11, Y' | Vollrath et al. (1988) |
| YCF4 | Ap$^r$, URA3, SUP11, CEN4, Y' | Vollrath et al. (1988) | b) Genetic and molecular techniques

Standard DNA methods were performed as described [Maniatis et al. supra]. Mutagenesis and strain constructions with E. coli were performed as described by Miller, Experiments in molecular genetics, Cold Spring Harbor Laboratory, Cold Spring Harbor, N.Y. (1972). S. cerevisiae was transformed as described by Beggs, in Nature Vol. 275:104–108 (1978) or Ito et al., in J. Bacteriol. Vol. 153:163–168 (1983). Crosses and strain constructions were performed using standard techniques [Sherman et al., supra]. Transposon shuttle mutagenesis and physical mapping by chromosome fragmentation were performed as described by Hoekstra et al. in Methods in Enzymology Vol. 194:329–342 (1991) and Vollrath et al. in Proc. Natl. Acad. Sci. Vol. 85:6027–6031 (1988), respectively.

c) PAD enzyme assay

Enzyme activity was assayed with permeabilized yeast cells. Cells grown to early stationary phase were washed once in 0.1 M phosphate buffer, pH 6.0, frozen in liquid nitrogen and lyophilized in screw cap tubes. The cells were resuspended in 1 ml 0.1 M Na phosphate buffer, pH 6, and the reaction initiated by adding 1 mM of sodium salt of substrates and incubating at 30° C. for 1 hour. The reaction was stopped by plunging the tubes in liquid nitrogen and adding KOH and NaCl to 2 M and 0.8 M, respectively. Products were then extracted with 5 ml n-hexane or diethylether with 10 $\mu$M 2,6-di-tert-butyl-4-methyl phenol. Ether was removed under vacuum in darkness and products taken up in 5 ml methanol. After HPLC on a RPC-18 column with 95% methanol as mobile phase, styrenes were quantified by UV absorption. Results are summarized in FIG. 1, where lane 1 illustrates the conversion of cinnamic acid to styrene, lane 2 illustrates the conversion of p-coumaric acid to 4-hydroxy styrene, lane 3 illustrates the conversion of ferulic acid (4-hydroxy-3-methoxy cinnamic acid) to 4-hydroxy-3-methoxy styrene, and lane 4 illustrates the conversion of 2-hydroxy cinnamic acid to 2-hydroxy styrene.

d) Decarboxylase activity in yeast

Decarboxylase activities were determined in a whole cell assay. Cells were permeabilized by lyophilization and incubated with substrate, the reaction products extracted into organic phase and separated on HPLC. The products were quantified by UV absorption; their authenticity confirmed by UV spectroscopy of the peak fraction. Additionally, $^1$H NMR spectroscopy confirmed styrene to be the reaction product when t-cinnamic acid was the substrate. The results show that t-cinnamic, p-coumaric, and ferulic acids were utilized with similar efficiency, giving rise to styrene, 4-hydroxy styrene, and 4-hydroxy-3-methoxy styrene, respectively. However, 2-hydroxy cinnamic acid, which does not occur in nature, was not decarboxylated with high efficiency. Thus, the observed decarboxylase activities were termed "phenylacrylic acid decarboxylase" (PAD).

e) Isolation and characterization of pad1 mutants

Mutants with reduced PAD activity were isolated after MNNG mutagenesis of yeast strain GRF18 [see Guthrie and Fink in Methods in Enzymology 194 (1991)]. Mutants were selected for sensitivity to growth inhibition in the presence of t-cinnamic acid, and for respiratory proficiency. Residual enzyme activity present in some of the pad mutants when grown on YM is shown in Table 3. When grown on complete medium, however, residual activities were higher and in the range of 25 to 50% of wildtype levels.

These mutants were backcrossed with the wildtype strains 6657-9B and a ura3 ws (see Table 2). The pad progeny issued from these crosses were further analyzed. All diploids issued from crosses between independent mutants were sensitive to growth inhibition in the presence of t-cinnamic acid, revealing the existence of a single complementation group. Heterozygous PAD/pad1 diploids were resistant to the effects of cinnamic acid, indicating the recessive nature of the mutation. This confirms the assignment of PAD to a single nuclear gene previously made by Goodey and Tubb [J. General Microbiol. 128:2615–2620 (1982)].

TABLE 3

Activity of phenylacrylic acid decarboxylase in different yeast mutants and transformants

| Yeast strain | Transformed with plasmid | specific activity [nM Styrene/ mg dm · h] | activity relative to wildtype (GRF18 = 100) |
| --- | --- | --- | --- |
| GRF18 | — | 3.7 | 100.0 |
| PDY102 | — | 0.8 | 21.9 |
| PDY102 | pPAD40 | 26.2 | 707.0 |
| PDY102 | pPAD133 | 29.4 | 795.0 |
| PDY192 | pPAD134 | 26.5 | 715.0 |
| z07 | — | 0.0 | 0.0 |
| z07 | pPAD150 | 60.0 | 1620.0 |
| z07 | pPAD151 | 61.0 | 1648.0 |
| z042 | — | 0.0 | 0.0 |
| z042 | pPAD150 | 40.1 | 1084.0 |
| z042 | pPAD151 | 41.6 | 1125.0 |
| z049 | — | 0.9 | 25.6 |
| z049 | pPAD150 | 43.1 | 1162.0 |
| z049 | pPAD151 | 61.1 | 1649.0 |
| z0107 | — | 0.7 | 19.6 |
| z0107 | pPAD150 | 62.2 | 1680.0 |
| z0107 | pPAD151 | 63.4 | 1710.0 |
| z0124 | — | 1.3 | 36.8 |
| z0124 | pPAD150 | 48.9 | 1321.0 |
| z0124 | pPAD151 | 50.1 | 1352.0 | f) Isolation and characterization of the PAD1 gene

The PAD1 gene was isolated by complementation of the pad1, ura3 strain PDY102 to cinnamic acid resistant phenotype after transforming this strain with a yeast genomic library [Carlson and Botstein, Cell Vol. 28:145–154 (1982)]. A primary selection for uracil prototrophy followed by selection for resistance to cinnamic acid resulted in the isolation of three independent transformants: pPAD24, pPAD40 and pPAD48. Cinnamic acid resistance and uracil prototrophy were simultaneously lost when transformed yeast cells were grown under non-selective conditions.

Plasmid DNA from these transformants was rescued into E. coli and subjected to restriction analysis (FIG. 2A). In the top panel of FIG. 2A, a detailed restriction map of the HindIII fragment complementing pad1 mutants to cinnamic acid resistance is presented. In the bottom panel of FIG. 2A, a map compiled from the analysis of three plasmids (pPAD24, pPAD40 and pPAD48) originally isolated from the genomic library is presented.

To delimit complementing activity, different BamHI and HindIII fragments were subcloned into pEMBLY23 and reintroduced into PDY102. See FIG. 2B, which provides a complementation analysis of fragments subcloned into pEMBLY23 (pPAD107, 111, 115, 133) after transformation into PDY102 or pYEplac181 (pPAD15, 16, 17, 18 and 19) [Gietz and Sugino, Gene Vol. 74:527–534 (1988)] after transformation into z042. Transformants were replica plated onto selective plates and phenotype scored after 3 days. Bidirectional arrows in FIG. 2B indicate that complementation analysis was performed with inserts cloned in both orientations. No differences were observed when fragments were assayed in both orientations. Only a 5.1 kb HindIII fragment restored wildtype phenotype (pPAD133). This fragment was ligated into pDB262, giving rise to plasmids pPAD150 and pPAD151 respectively. All of the originally isolated mutant strains transformed with these plasmids displayed restored wildtype phenotype (see Table 3), indicating that complementation was not allele-specific.

g) Localization of PAD1 on the 5.1 HindIII fragment

A more precise localization of the PAD1 gene on the 5.1 kb HindIII fragment was performed by three different methods: in vivo generated deletions, transposon mutagenesis and complementation analysis with smaller restriction fragments.

Deletions were generated in vivo by selecting for fusions to the *E. coli* lacZ gene. The 5.1 kb HindIII fragment was cloned upstream of a promotorless lacZ gene (i.e., into the HindIII site of YEpZ100 [Oberto and Davison, Gene Vol. 40:57–65 (1985)], which is located 5' of the lacZ open reading frame) in both orientations, resulting in plasmids pZYC and pZYD. These plasmids were introduced into the lac⁻ *E. coli* strain AMA 1004 and lac⁺ clones (harboring in vivo generated deletion plasmids) were selected by testing for growth on lactose as sole carbon source [Rose and Botstein, Meth. Enzymol. Vol. 101:167–180 (1983)]. Deletion plasmids were purified once by transformation into PDC75 to preclude effects in trans from undeleted plasmids still present in some clones. The extent of the deletion was determined by restriction mapping, after which the plasmids were introduced into *S. cerevisiae* z042 for determination of PAD activity (see Table 4). Restriction analysis of plasmids isolated from these clones confirmed that yeast sequences had been deleted (FIG. 3B). Measurements were done in quadruplicate.

TABLE 4

Enzyme activities expressed from fusion plasmids in *S. cerevisiae* z042

| Plasmid | Phenylacrylic acid decarboxylase | |
|---|---|---|
| | Specific activity [nM Styrene/mg dm · h] | relative to wt (%) |
| pZYDs25 | 44.25 | 80.9 |
| pZYDs51 | 4.94 | 9.0 |
| pZYDs35 | 1.25 | 2.3 |
| pZYCs12 | 53.21 | 97.4 |
| pZYCs20 | 45.32 | 82.9 |
| pZYCs19 | 1.40 | 2.6 |
| pZYDs41 | 1.49 | 2.7 |
| pZYC | 53.85 | 98.5 |
| pZYD | 55.47 | 102.0 |

Activity is reduced by less than 20% when 1.3 kb and 0.9 kb are deleted from the right and left ends of the 5.1 kb HindIII fragment, respectively. It can be concluded that the PAD1 gene is located between the deletion endpoints in plasmids pZYDs25 and pZYCs20.

Transposon mutagenesis as described by Hoekstra et al. supra was used to map the PAD1 gene with greater precision within this interval. Briefly, the 5.1 kb HindIII fragment was cloned into pHSS8 in both orientations, giving rise to pPAD5 and pPAD6. These plasmids were introduced into *E. coli* RDP146 (pLB101), where transposition of a defective mini-transposon carrying a functional LEU2 gene into the plasmids occurred. Transformants were mated with RDP146 (pOX38::mTn3-LEU2) and transconjugants carrying all three plasmids were selected. Transposition of the resident mini-transposon carrying a functional LEU2 gene into pPAD5 and pPAD6 was then allowed to occur. Co-integrate structures were then resolved by Cre mediated site specific recombination at loxP sites, accomplished by mating with *E. coli* NS2114Sm. Mutant plasmids were purified and the insertion sites were mapped. The resulting plasmids were almost exclusively mutant in insert sequences disrupted by the LEU2 gene.

Plasmids with mutant inserts were linearized and used to transform wild-type yeast to leucine prototrophy. LEU⁺ yeast transformants were selected after transformation of GRF18 with linearized plasmid DNA. In these LEU⁺ transformants, the endogenous 5.1 kb HindIII fragment had been replaced with sequences disrupted by the transposon insertion. This was verified by Southern analysis of DNA isolated from transformants. Transformants were assayed for resistance to cinnamic acid. Integration sites that did not destroy resistance to cinnamic acid are shown hatched in FIG. 3A, and those sites that resulted in cinnamic acid sensitive transformants are shown in FIG. 3A in white. Yeast cells transformed with DNA from plasmids 5-15, 6-4 and 5-11 remained resistant to cinnamic acid, whereas cells transformed with 5-16, 5-9, 5-3, 5-13, 6-6 and 6-8 DNA became sensitive to cinnamic acid. The results, summarized in FIG. 3A, show that disruption within a 2.3 kb region around the BamHI site destroys resistance to growth inhibition by cinnamic acid.

These results were confirmed by complementation analysis with smaller restriction fragments of the 5.1 kb HindIII fragment cloned into the high copy number vector YEplac181. The smallest fragment complementing PDY102 to wildtype levels of cinnamic acid resistance was a HindIII-StuI fragment (FIG. 2B).

Taken together, the results obtained by three different experimental approaches indicate that pad1 complementing activity can be localized to a region approximately 2.3 kb in size surrounding the BamHI site.

h) Subcellular localization of the enzyme

The subcellular location of phenylacrylic acid decarboxylase (PAD) activity in yeast was determined after subjecting gently ruptured yeast protoplasts to differential centrifugation. Protoplast homogenates were prepared by digesting yeast cell walls in isotonic buffer as described by Beggs supra. Protoplasts were then resuspended in 0.4 M sorbitol, 20 mM Tris·Cl pH 7.5, 5 mM $MgCl_2$, 1 mM PMSF, after which two volumes of the same buffer with only 0.1 M sorbitol were added. The swollen protoplasts were then disrupted in a teflon pestle homogenizer. The resulting protoplast homogenate was subjected to differential centrifugation as described by Perlman and Mahler, Arch. Biochem. Biophys. Vol. 136:245–259 (1970).

The fractions from centrifugation were assayed for PAD, glutamate dehydrogenase (GDH) and cytochrome c oxidase (COX) as markers for cytoplasmic and mitochondrial localization, respectively (see Table 5). Assays for glutamate dehydrogenase (GDH) and for cytochrome c oxidase (COX) were carried out as described by Polakis and Bartley, Biochem. J. Vol. 97:284–297 (1965) and Mason et al., J. Biol. Chem. Vol. 248:1346–1354 (1973) respectively. The assay for PAD was performed as described above. Protein was determined by the method of Bradford, Anal. Biochem. Vol. 72:248–254 (1976).

After a low speed spin to eliminate debris, the highest level of PAD activity was recovered from the supernatant of the 20 k× g fraction. The distribution of PAD activity paralleled the distribution of GDH, indicative of a cytoplasmic location for the PAD protein.

TABLE 5

Recovery of enzyme activities after differential centrifugation of a protoplast homogenate

| | Recovery, % | | |
|---|---|---|---|
| Cellular fraction | PAD | GDH | COX |
| Protoplast homogenate | 100 | 100 | (100) |
| Supernatant of 600 g | 63 | 73 | 81 |
| Pellet from 600 g | 10 | 11 | 19 |
| Supernatant of 20000 g | 59 | 67 | 10 |
| Pellet from 20000 g | 2 | 0 | 41 |

Example 13

Effect of expression of yeast PAD in plants

After determining by Southern blot analysis that the genomes of tobacco, *Arabidopsis thaliana*, and bean, taken to represent average higher plants, do not contain PAD homologous sequences, the yeast PAD gene (isolated as described above) was introduced into both tobacco (see Examples 1 and 2 for procedures) and Arabidopsis by T-DNA mediated transformation [see, for example, Valvekens et al., in Proc. Natl. Acad. Sci. USA 85:5536–5540 (1988)]. For these transformations, several different constructs were generated with the expression of the PAD gene placed under the control of different promoters:

(a) the constitutive, viral 35S promoter;

(b) the vascular predominant bean PAL2 promoter; and (c) the vascular specific bean GRP 1.8 promoter.

Successful transformation was selected for by identifying drug resistant regenerating plants. This is accomplished as follows:

Southern Blot analysis of plants using the GRP 1.8 promoter-PAD gene fusion indicates that several independent putative transgenic lines (selected for by the drug resistance marker) contain the PAD gene in single or multiple copies.

Northern Blot analysis indicates expression of the yeast PAD gene occurs in tobacco under the control of both the 35S and the PAL2 promoters. The highest levels of expression were observed in a transgenic line with two or multiple linked inserts of PAD under the control of the strong 35S promoter.

Results regarding the copy number of the introduced transgene were confirmed by segregation analysis of the linked drug resistance marker.

The effect of the introduced PAD gene can be observed in a variety of ways. Late in development of a transgenic line carrying two unlinked insertion sites of the transgene with the PAD gene under the control of the 35S promoter, the leaves show a wilting phenotype consistent with reduced water transport within the plant. Since the vascular system of the plant is a primary site for lignification within the plant, the most revealing effects of reduced lignification levels caused by the presence of PAD are likely to be observed here.

Stem cross sections of mature plants from this line show a statistically significant reduction in the percentage of the lignified area. This observation suggests a reduction in the extent of vascular development.

The analysis of transpiration (indicative of the rate of water loss per unit leaf area) and the rate of photosynthesis (a good diagnostic for how the plant senses water activity within the cells) indicate the transgenic plants have lower rates of transpiration and less photosynthetic activity. These observations are also consistent with reduced lignification levels in the transgenic plant.

While the invention has been described in detail with reference to certain preferred embodiments thereof, it will be understood that modifications and variations are within the spirit and scope of that which is described and claimed.

---

That which is claimed is:

1. A method for producing PAD in a plant comprising:

transforming said plant with a PAD gene, and expressing said PAD gene in said plant.

2. A method according to claim 1, wherein said plant is transformed with a construct comprising said PAD gene under the control of a suitable promoter.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (v) FRAGMENT TYPE: N-terminal (xi) SEQUENCE DESCRIPTION: SEQ ID NO:1:

Gly Arg Ile Phe Glu Ile Leu Glu Ala
1               5

(2) INFORMATION FOR SEQ ID NO:2:

(i) SEQUENCE CHARACTERISTICS:
        (A) LENGTH: 9 amino acids
        (B) TYPE: amino acid -continued

```
        (C) STRANDEDNESS: single
        (D) TOPOLOGY: linear (ii) MOLECULE TYPE: peptide (v) FRAGMENT TYPE: N-terminal (xi) SEQUENCE DESCRIPTION: SEQ ID NO:2:

Gln Ile Glu Ala Ala Ala Ile Met Glu
1               5
```